United States Patent [19]
Gold et al.

[11] 4,004,344
[45] Jan. 25, 1977

[54] DENTAL DEVICE

[76] Inventors: Gary K. Gold, 5065 Stoneboat Row, Columbia, Md. 21044; Alan H. Hart, 3204 Hatton Road, Pikesville, Md. 21208

[22] Filed: Sept. 4, 1975

[21] Appl. No.: 610,290

Related U.S. Application Data

[63] Continuation of Ser. No. 503,678, Sept. 6, 1974, abandoned.

[52] U.S. Cl. .................................. 32/27; 32/59
[51] Int. Cl.² .................................. A61C 1/10
[58] Field of Search ............... 32/59, 27; 15/23, 24, 15/28, 29; 128/56; 310/47, 50

[56] References Cited
UNITED STATES PATENTS

| | | | |
|---|---|---|---|
| 2,911,660 | 11/1959 | Klemas et al. | 128/56 X |
| 3,380,162 | 4/1968 | Heathe | 32/27 |
| 3,509,629 | 5/1970 | Kidokoro et al. | 32/27 |

*Primary Examiner*—Robert Peshock
*Attorney, Agent, or Firm*—Morton J. Rosenberg

[57] ABSTRACT

A dental device for removing stains from teeth which includes a housing easily maintained, manipulatable, and operable in one hand of an operator. The housing includes a head member having a first internal chamber and a longitudinally extended handle member defining a second internal chamber. A motor is mounted within the first internal chamber of the head member and is directly connected in rotative displacement to a rubber cup stain removing element which is coupled to the motor external to the housing head member. In one form of the dental device the motor is electrically connected to a pair of batteries which are mounted within the second chamber of the handle member. Operation of the motor is provided by a switch which passes external to the housing and is actuated by one finger of the operator. When actuated, the switch completes an electrical path between the batteries and the motor in order to generate rotative displacement of the rubber cup which serves as the stain removal mechanism from the teeth of the user.

8 Claims, 6 Drawing Figures

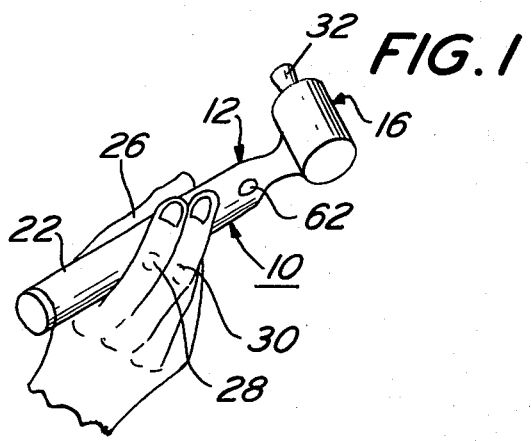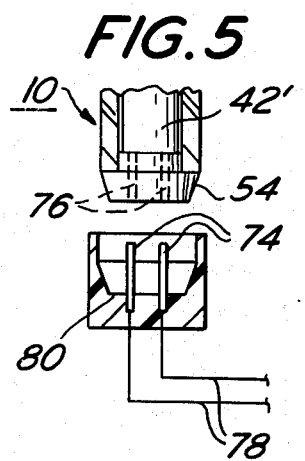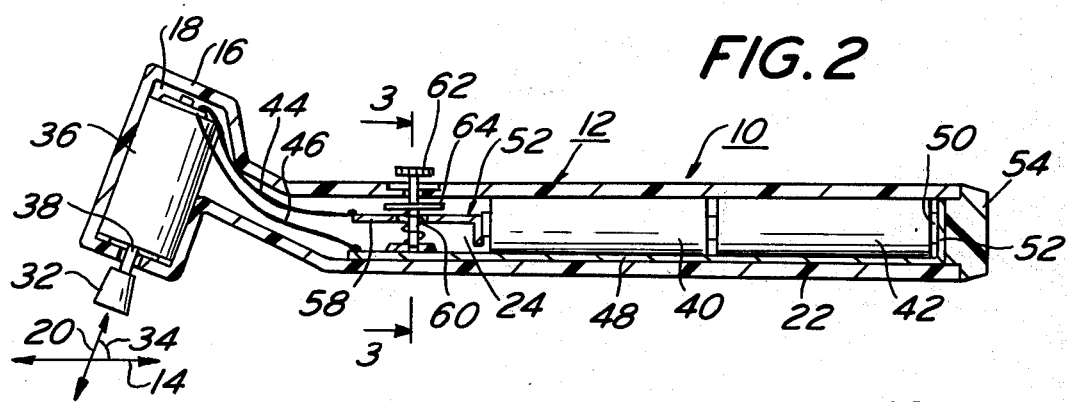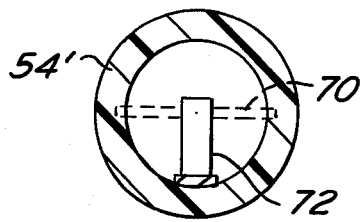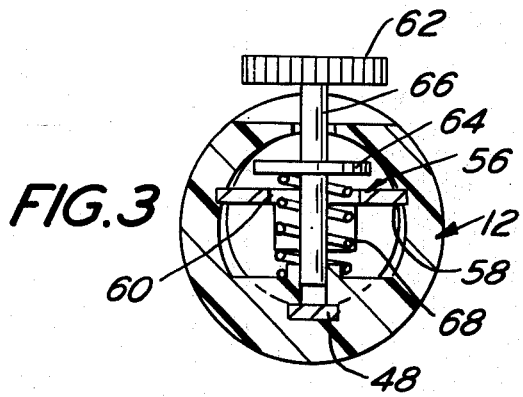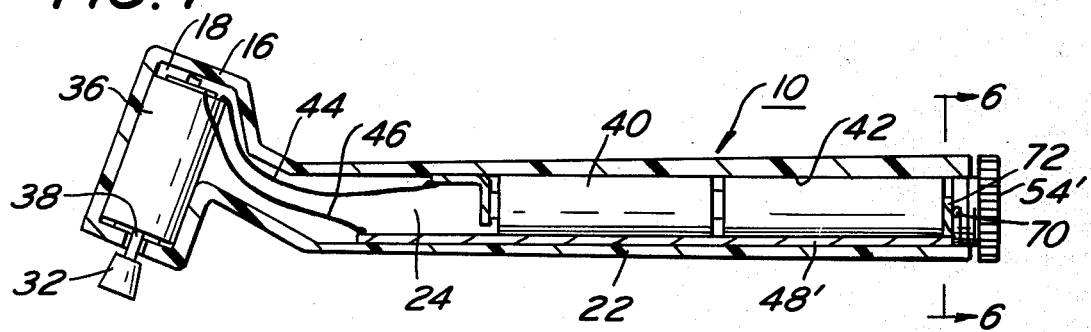

DENTAL DEVICE

This is a continuation of application Ser. No. 503,678, filed Sept. 6, 1974 and now abandoned.

BACKGROUND OF THE INVENTION

Field of the Invention

This invention pertains to dental devices. In particular, this invention relates to dental devices for use in removing stains from teeth. More in particular, this invention pertains to a dental device for removing stains from the teeth of a user which is easily manipulatable in one hand and is of a portable nature. Still further, this invention relates to a dental device which is geometrically contoured in optimized fashion for easy manipulation by an operator. Additionally, this invention relates to a dental device which can be held in one hand by an operator throughout the stain removing process and be actuated by one finger. Further, this invention pertains to a dental stain removing device which can be used in the home by an operator for periodic removal of stains from his or her teeth.

Prior Art

Dental devices for removing stains from teeth are well known in the art. However, some of the prior art dental devices include motors which are mounted in the handle portion of the particular device. Such devices, by necessity, include large internal handle volumes resulting in complex kinematic linkages passing from the motor to the stain removing member. Such kinematic linkages, increase the manufacturing costs of these prior devices and in some cases have been found to reduce the reliability of these prior devices.

Additionally, in such devices where the motor is maintained in the handle section of the dental device, manipulation in one hand of the user is extremely difficult. Thus, the operator uses an unnatural and uncomfortable motion in removing the stains from the teeth. In such devices, a certain amount of skill is needed to optimize the stain removing capacity of such prior devices which inherently decreases the number of people who can use these prior devices effectively.

Further, the increased volume in the handle member due to the motor and associated linkage mechanisms restricts the portability of such prior devices and generally has not permitted the user to easily carry such dental devices with him or her during their normal course of business.

Additionally, in some prior devices, the head member is directed substantially normal to the handle portion of the dental device. Such geometric contouring provides for an unnatural motion in the cleansing of anterior teeth of an operator and may affect the dental stain removing process.

Further, even where a motor may be inserted in the head member of some prior dental devices, such devices do not provide for an actuating switch in the handle section of the dental device which allows for use and operation of the dental device with one finger of the operator. In such cases, the motor mechanism may be affected through over extended use of the battery or other electrical source means.

SUMMARY OF THE INVENTION

A dental device for removing stains from teeth which includes a housing having a head member forming a first chamber and a longitudinally extended handle member forming a second chamber. A motor mechanism is mounted within the first chamber of the head member. An electrical power source is coupled to the motor mechanism which is rotatively coupled to a stain removal member. A mechanism for actuating the stain removal member in rotative displacement is mounted in the longitudinally extended handle member of the housing.

BRIEF DESCRIPTION OF THE DRAWINGS

FIG. 1 is a perspective view of the dental device being held in one hand of an operator;

FIG. 2 is a cut-away view of the dental device showing the internal elements;

FIG. 3 is a sectional view showing the switching member taken along the section line 3—3 of FIG. 2;

FIG. 4 is a cut-away side view of an embodiment of the dental device showing the internal elements where the switching member is formed in a cap section of the dental device;

FIG. 5 is a partial cut-away view of an embodiment of the dental device showing adaptation of the dental device for use with rechargeable batteries; and, FIG. 6 is a sectional view of the embodiment shown in FIG. 4 taken along the section line 6—6 of FIG. 4.

DESCRIPTION OF THE PREFERRED EMBODIMENTS

Referring now to FIGS. 1, 2 and 3, there is shown dental device 10 for use by an operator or user in removing stains from teeth. As will be described in detail in following paragraphs, device 10 provides an effective dental appliance which is sanitary, light in weight and convenient for use in the home. In overall concept, dental device 10 is designed to remove stains from the facial surfaces of a user's anterior teeth which has developed over a period of time. Device 10 has been found effective in removing stains developed on the anterior teeth from smoking, drinking coffee, tea, etc. Additionally, dental device or stain removing mechanism 10 has been designed to allow use by an operator without professional training and is intended to be easily manipulatable by a user in one hand.

Dental device 10 includes housing 12 which is generally extended in a longitudinal direction defined by directional arrow 14 shown in FIG. 2. Housing 12 is formed of head member 16 defining first internal chamber 18, contoured to accept motor 36 to be further described. Head member 16, as is shown in FIGS. 1 and 2 is generally cylindrical in overall shape and is extended in a predetermined direction as defined by directional arrow 20 taken with respect to longitudinal direction 14. Housing 12 also includes longitudinally extended handle member 22 also having a generally cylindrical outer contour although such is not important to the inventive concept as is herein detailed. Handle member 22 includes second chamber 24 for containing other working elements to be further described. In use, dental device 10 is gripped about handle member 22 between an operator's thumb 26, fore finger, and index fingers 28, 30 as is shown in FIG. 1. In this manner, handle member 22 is gripped by a user similar to the gripping action used in holding a pen or pencil.

This type of gripping action optimizes the dexterity of manipulation of device 10 and is basically the same grip action used by dentists in controlling a "cavitron" insert.

Actuation of device 10 provides for rotative displacement of rubber cup 32 which is placed in contact with the anterior teeth of the user to remove the previously described stains through abrasive removal after cup 32 has been coated with a standard polishing paste, well known in the art. It is the need for easy manipulation of device 10 as is shown in FIG. 1 which necessitates that the outer diameter of handle member 22 be optimized to a reduced dimension such that manipulation of the device 10 can be accomplished in one hand. Handle member 22 has a preferred outer diameter approximating 0.50 inches for ease of manipulation by a wide range of operators in one hand during the stain removing process. The importance of the outer diameter of handle member 22 is seen in that once a reduced optimized dimension has been ascertained, such dictates the allowable mechanisms and their positional location internal to dental device 10.

Also of importance in determining the ease of manipulaton by the operator of dental device 10 when in use by an operator is angle 34 made by the intersection of predetermined direction 20 and longitudinal direction 14 as is shown in FIG. 2. Although highly dependent on the individual using dental device 10, it has been found that optimized results for a wide variety of operators have been found when angle 34 approximates 50°. However, angle 34 has been formed in angles approximating the range of between 45°–90° with varying degrees of success generally based on individual requirements.

Additionally, housing 12 formed of head member 16 and handle member 22 may be constructed in molded one piece fashion to provide a relatively low cost, easily manufacturable housing 12. Additionally, housing 12 is generally formed of a plastic like material which is chemically inert to human saliva and human contaminant generally found in the mouth. Such material may generally be polypropylene or some like material.

As is shown in FIG. 2, motor 36 is mounted within first chamber 18 of head member 16. In general, motor 36 is a light weight, low torque motor which allows reduced or complete stoppage of rotative displacement when a large force or pressure is exerted between rubber cup 32 and the teeth of the user. In general, a number of well known motors 36 may be used, one of such motors being used with success is Marx Microperm, Type 6000, Voltage 1–4 volts, 240Ma–1.3A. Motor 36 is secured to rubber cup 32 in a removable manner through motor shaft 38. Actuation of motor 36 causes rotative displacement of motor shaft 38 with a resultant concurrent rotation of rubber cup 32 which is resiliently fixed on one end of motor shaft 38 as is shown in FIG. 2. Thus, rubber cup 32 which interfaces with the operator's teeth for stain removal purposes defines the stain removal means which is rotatively coupled to motor 36 through motor shaft 38.

In the preferred form of the invention shown in FIG. 2, power to actuate motor 36 is provided by a pair of batteries 40 and 42. Batteries 40 and 42 are mounted in handle member 22 within second chamber 24 as is shown. One set of batteries 40 and 42 now being used are size AAA, 1.5 volts, No. E92 produced by Union Carbide Corporation. Such batteries 40, 42 permit an internal diameter of second chamber 24 approximating ⅜ inch. Batteries 40, 42 as are seen in FIG. 2 are positionally located in consecutive alignment in longitudinal direction 14 in order to maintain the external diameter of handle member 22 in an optimized reduced dimension for ease of manipulation in one hand of an operator.

Motor 36 is electrically connected to batteries 40 and 42 through motor lead wires 44, 46. Lead wire 46 is connected on opposing ends thereof to motor 36 and metal conductor 48 which passes in substantially longitudinal direction 14 along an inner wall of second chamber 24 of handle member 22. Metal conductor 48 passes to a rear portion of second chamber 24 and is placed in electrical contact with battery 42 through electrical contact member 50. Metal conductor 48 may be an end piece of electrically conducting metal, electrically conducting wire or some like element which permits a low electrical resistance to permit the flow of electricity. It will be noted that contact member 50 may be mounted to electrical conductor 52 on one end of cap member 54 as is shown in FIG. 2. In this form, electrical conductor 52 provides a path between contact member 50 and metal conductor 48. However, a number of electrical path elements may be devised by those skilled in the art, with the important concept being that an electrical path be provided between motor 36 and a rear face of battery 42 to provide the necessary electrical flow.

Cap member 54 may be mounted within handle member 22 in a variety of methods. One such mounting may be through force fit, however, cap member 54 may also be threadedly engaged to second chamber 24 within handle member 22. The manner and mode of the attachment of cap member 54 within second chamber 24 not being critical to the inventive concept of the invention as is herein detailed with the exception that the mounting utilized provide for the necessary electrical path.

Rotative operation of stain removal member or rubber cup 32 is maintained through actuation of switch mechanism 56. As is seen, lead wire 44 is mounted on opposing ends to motor 36 and lug member 58 of switch mechanism 56. Lug member 58 includes opening 60 which interrupts the electrical path between motor 16 and battery 40. Displacement of button 62 in a downward direction substantially normal to longitudinal direction 14 causes contact between electrical conductor 64 and a lug member 58 to complete an electrical path and actuate motor 36. Conductor 64 is secured in fixed constrainment to button shaft 66 as is shown in FIGS. 2 and 3. Helical spring member 68 biases button element 62 in a non-electrical contact position as is shown.

Thus, the user while gripping handle member 22 with one hand may actuate motor 36 by depressing button element 62 with one finger 28 or 30. Release of button element 62 by the operator causes immediate stoppage of motor 36 with a resultant stoppage of the rotative displacement of stain removal or rubber cup 32.

An embodiment of dental device 10 is shown in FIGS. 4 and 6 where the mechanism for actuating stain removal element 32 is placed in cap member 54' as is seen in FIG. 6, cap 54' has embedded therein contact pin 70 which is electrically conductive and interfaces in contiguous contact with electrical contact member 72. Contact member 72 is in contiguous contact with a rear end of battery 42. In this embodiment, contact pin 70 is rotated until it touches metal conductor 48' which then provides a path from motor 36 through lead wire 46, metal conductor 48', contact pin 70, contact member 72 and battery 42. Thus, in this embodiment actuation means or the switch member for operational purposes is provided in handle member 22 at a rear portion thereof. Rotative displacement of contact pin 70 into contact with metal conductor 48' provides for the necessary electrical path for operation of rubber cup 32 as has been previously described.

Still another embodiment of dental device 10 is shown in FIG. 5 where battery 42' is of the rechargeable type. In this embodiment, base mount member 80 includes male plug members 74 coupled to cord 78 which is connected to an energy source which is not shown. Electrical plug members 74 are inserted in female recepticals 76 formed within cap member 54 in order to provide an electrical path to rechargeable battery 42'. In this manner, dental device 10 may still be portable and used freely without resorting to the constrainment of electrical wires being plugged into an electrical energy outlet. After batteries 42' have been electrically dissipated, device 10 may be inserted within plug members 74 of base mount 80 and recharged by insertion of cord 78 in a standard electrical outlet. Such rechargeability of batteries 42' and mechanisms therefore are well known in the art, one such being shown in U.S. Pat. No. 3,757,419.

In another form of the invention, motor 36 within device 10 may be electrically connected directly to a standard electrical outlet which would dispense with the use of batteries 40, 42. However, in such embodiment, portability of device 10 would in some ways be effected since the user would be limited to the extension length of the electrical outlet cord. Further, in such cases the user would be restricted to the proximity of an electrical outlet.

It is evident from the foregoing description of the illustrative embodiments of this invention that various modifications can be employed by those skilled in the art to which this invention pertains. Accordingly, it is intended that the instant invention be limited only in the manner described by the appended claims.

What is claimed is:

1. A dental device for removing stains from teeth comprising:
   a. a housing having a head member extending in a predetermined direction forming a first chamber and a longitudinally and linearly extended handle member forming a second chamber, said extended handle member adapted to be gripped between an operator's thumb, index and fore fingers said handle member and said head member being formed in one piece construction, said extended directions of said head and handle member forming an angle approximating 50° therebetween;
   b. motor means mounted within said first chamber of said head member said first chamber being contoured to receive only said motor means;
   c. electrical power means coupled to said motor means said electrical power means being mounted within said extended handle member second chamber;
   d. stain removal means rotatively coupled directly to said motor means in linear alignment through rotative securement to a rigid shaft member passing through said head member of said housing, said shaft member being opposingly mounted only to said stain removal means and said motor means, said shaft member having an extended length substantially less than said head member whereby said stain removal means may be easily manipulated at varying angles when contacting said teeth; and
   e. means for actuating said stain removal means in rotative displacement, said actuation means being mounted in said longitudinally extended handle member of said housing adjacent said head member in positional placement for actuation by one finger of said operator while said handle member is being gripped.

2. The dental device as recited in claim 1 where said handle member includes an outer diameter approximating 0.50 inch for ease of manipulation by an operator in one hand.

3. The dental device as recited in claim 1 where said housing is formed of a plastic material being chemically inert with respect to human saliva.

4. The dental device as recited in claim 1 where said electrical power means includes at least one battery means mounted within said second chamber of said handle member for providing electrical power to said motor means.

5. The dental device as recited in claim 4 incuding means for electrically recharging said battery means, said recharging means being releaseably connectable to said battery means and an external electrical power source on opposing ends thereof.

6. The dental device as recited in claim 1 where said means for actuating said stain removal means includes switch means for electrically connecting said motor means to said electrical power means for rotatively driving said stain removal means.

7. The dental device as recited in claim 6 where said switch means is biased in an electrical disconnect position, said switch means passing through a wall of said housing for movement in a direction substantially normal to said longitudinal extension by one finger of an operator for displacing said switch means to an electrical connect position for actuating said motor means.

8. The dental device as recited in claim 1 where said stain removal means includes rubber cup means releasably mounted to said motor means, said rubber cup means extending through a wall of said head member and rotatively displaceable with respect thereto.

* * * * *